United States Patent [19]
Shigemitsu

[11] Patent Number: 4,647,537
[45] Date of Patent: Mar. 3, 1987

[54] IMMOBILIZATION OF MICROORGANISMS ANTAGONISTIC TO PLANT PATHOGENIC MICROORGANISMS

[75] Inventor: Haruhiro Shigemitsu, Nagoya, Japan

[73] Assignee: Sumitomo Forestry Co., Ltd., Japan

[21] Appl. No.: 643,431

[22] Filed: Aug. 23, 1984

[30] Foreign Application Priority Data

Feb. 27, 1984 [JP] Japan .................. 59-35561

[51] Int. Cl.$^4$ .................. C12N 11/10; C12N 11/14; C12N 11/02
[52] U.S. Cl. .................. 435/178; 435/176; 435/177
[58] Field of Search .............. 435/174, 176, 177, 178, 435/180, 182

[56] References Cited

U.S. PATENT DOCUMENTS

| | | | |
|---|---|---|---|
| 3,989,597 | 11/1976 | Lee et al. | 435/174 |
| 4,138,292 | 2/1979 | Chibata et al. | 435/178 |
| 4,433,054 | 2/1984 | Chibata et al. | 435/178 |

FOREIGN PATENT DOCUMENTS

| | | | |
|---|---|---|---|
| 6884 | 1/1984 | Japan | 435/182 |

OTHER PUBLICATIONS

Sato, et al., Biochimica et Biophysica Acta, vol. 570, 1979, pp. 179–186.
Pitcher Jr., Witt., Immobilized Enzymes for Food Processing, CRC Press Inc., Florida, 1980, pp. 2–3.
*Enzyme Engineering* (Kogaku Publication) edited by S. Fukui et al., 1981, pp. 1–17.

*Primary Examiner*—David M. Naff
*Attorney, Agent, or Firm*—Banner, Birch, McKie and Beckett

[57] ABSTRACT

A method is disclosed for preparing an immobilized microorganism-complex having controlling activity against plant pathogenic microorganisms. The method comprises adding an inorganic salt of a polyvalent metal to a liquid containing microorganism cells antagonistic to plant pathogenic microorganisms, drying the resulting microorganism cells so as to obtain a powder, mixing the powdered microorganism cells with particles of humic acid obtained by extraction from compost to obtain aggregates of the microorganism cells, mixing the aggregates with an aqueous carrageenan solution, and then drying the resulting mixture.

4 Claims, No Drawings

IMMOBILIZATION OF MICROORGANISMS ANTAGONISTIC TO PLANT PATHOGENIC MICROORGANISMS

BACKGROUND OF THE INVENTION

This invention relates to a method for preparing an immobilized microorganism-complex having controlling activity against plant pathogenic microorganisms.

As the conventional methods for immobilizing cells of microorganisms, there have been known (1) carrier-bonding method, (2) bridging method and (3) entrapping method [Saburo Fukui et al. (Ed.), Kōso Kōgaku (Enzyme Engineering), pp 158–164]. These methods have all been used in an attempt to carry out a successive enzymatic reaction.

BRIEF DESCRIPTION OF THE INVENTION

The present inventor made extensive studies to improve the above-mentioned immobilization methods for the purpose of controlling plant diseases. Consequently, it has been found that a strong controlling effect against plant diseases can be obtained by a combination method of ionic bonding and entrapping methods. This invention has been accomplished on the basis of the above finding.

Thus, according to this invention, first humic acid is extracted from various composts in a known manner by using an alkalic or acid solution. Meanwhile, a microorganism antagonistic to plant pathogenic microorganisms (hereinafter referred to simply as microorganisms) is subjected in a conventional manner to shake culture or static culture in a liquid medium; the culture substance is pulverized together with the liquid medium using a mixer; an inorganic salt of a metal having a valency of two or more is added to the solution at a concentration of 0.1 M and allowed to react therewith; then the reaction mixture is subjected to spray-drying and the like to obtain the microorganisms in a powder form. Since the powdered microorganisms thus-obtained have a positive charge, when it is admixed well with humic acid, it attaches itself to the anionic particles of humic acid by ionic bond. The thus-obtained aggregate is mixed with an aqueous solution containing 10% W/W or more of carrageenan, and the resulting mixture is subjected to drying with stirring. A theoretical background of thus-obtained immobilized microorganisms is that the powdered microorganisms and humic acid are first bound by ionic bondage, and this binding form is entrapped by carrageenan.

There is no specific restriction as to the microorganisms to be used in this invention so long as they have antagonism against plant pathogenic microorganisms. Examples of usable ones include bacteria, actinomycetes, eumycetes, myxomycetes, lichens and algae. These microorganisms may be used not only in living form but also as lyophilized or thawed, living microorganisms.

The microorganisms to be used in this invention may be either of a single species or of two or more strains of the same species. Furthermore, two or more kinds of different species can also be used simultaneously.

The culture of the microorganism in this invention may be spores obtained by submerged culture and by solid culture.

The inorganic salts of bivalent or more metals (i.e., having a valency of two or more) used in this invention include, for example, calcium chloride, magnesium chloride, barium chloride, ferrous chloride, ferric chloride and manganese chloride.

The humic acid used in this invention include those extracted from compost of rice straw, barley or wheat straw, livestock excretions, bark, sawdust, activated sludge, urban wastes, or the like. Those extracted from soil may also be used.

Preferred examples of carrageenan to be used in this invention include "Newgelin" (trade name, mfd by Chuo Kasei Inc.), "Genugel WG" (trade name, mfd by Copenhagen Pectin Factory Inc.) and "Genugel CWG" (ditto).

The complex obtained according to the method of this invention exhibits a strong controlling effect against plant diseases, particularly soil-borne diseases, and moreover promotes the growth of plants, so that it can be particularly advantageous for cultivation of plants.

This invention will be illustrated in detail below with reference to Examples, but it is in no way limited thereto.

EXAMPLE 1

A culture medium containing 0.5% of peptone, 0.1% of potassium phosphate, 0.05% of magnesium sulfate and 1% of sucrose and having a pH of 7.0 was placed, in 100 ml portions, into 500 ml Sakaguchi-flasks and, after sterilization, inoculated with *Bacillus licheniformis* antagonistic to *Fusarium* spp, soil-borne plant pathogenic microorganisms, and subjected to shake culture at 28° C. After 3 days of incubation, calcium chloride was added to the culture liquid at a concentration of 0.1 M and allowed it to react with cells of the microorganisms. The resulting mixture was spray-dried to give 3 to 5 g of the powdered cells of the microorganism.

EXAMPLE 2

*Thermoactinomyces sp* antagonistic to *Fusarium spp*, soil-borne plant pathogenic microorganisms, was cultured in a culture medium for actinomycetes, and then dried in the same manner as in Example 1 to give 3 to 5 g of the powdered cells of the microorganism.

EXAMPLE 3

*Aspergillus terreus* and *Trichoderma viride* antagonistic to *Corticium rolfsii*, a soil-borne plant pathogenic microorganism, and *Penicillium sp* antagonistic to *Pseudomonas solanacearum* were subjected to shake culture, and the culture substance obtained was pulverized with a mixer. The resulting product was dried in the same manner as in Example 1 to give 3 to 5 g of the powdered cells of the microorganisms.

EXAMPLE 4

To 500 g of bark compost was added 1 liter of 0.15 M sodium pyrophosphate, and the mixture was allowed to stand for 48 hours with occasional stirring. The mixture was subjected to filtration using filter papers the resulting solution was brought to a pH of about 0.8 by addition of hydrochloric acid, and the precipitated humic acid was collected by centrifugation to give 100 to 150 g of humic acid.

EXAMPLE 5

1 g each of the 5 kinds of pulverous microorganisms prepared as in Examples 1 to 3 were added to 100 g of the humic acid and mixed thoroughly to form ionic bonds between the components. The aggregates thus-obtained were mixed with 500 ml of a 10 W/W % aqueous carrageenan solution, and the mixture was subjected to spray drying with stirring to give 100 to 120 g of immobilized microorganism comprising the microorganism and humic acid as a carrier.

EXAMPLE 6

The effect of the complex prepared in the same manner as in Example 5 on the growth of crops was examined. The results are as shown in Table 1. Cucumber was used as a test crop. The values indicated in the table are those obtained by inspection on the 14th day from sowing.

TABLE 1

| Test plot and concentration (g/15 cm pot) | Average height of 100 individual aerial parts (cm) | Dry weight of 100 individual aerial parts (g) | Dry weight of 100 individual subterranean parts (g) |
| --- | --- | --- | --- |
| Diluvial soil | 2.73 | 7.9 | 3.9 |
| Complex, 1 g | 6.13 | 10.2 | 5.9 |
| Complex, 2 g | 7.54 | 11.9 | 6.6 |
| Complex, 3 g | 7.71 | 13.0 | 6.2 |

EXAMPLE 7

The controlling effects of the complex prepared in the same manner as in Example 5 on Fusarium wilt of cucumber, Fusarium wilt of tomato and Bacterial wilt of eggplant were examined. The results are as shown in Table 2.

Thus, each of the pathogenic microorganisms was incubated and then inoculated to diluvial soil so that $5$–$6 \times 10^6$ microorganism cells would be present per 1 g of dry soil. Then the above-mentioned complex was mixed with the soil in a proportion of 1 g per pot of 15 cm in diameter. Cucumber, tomato and eggplant were then sown and grown in the pots, and the numbers of wilted and withered individuals of respective plants were examined. The control plot was the diluvial soil inoculated with the pathogenic microorganism. The experiments were carried out in 3 replicates by using 10 pots per plot, 10 seeds being sown in each pot.

The "control value" was calculated from the following formula:

Control value (%) =

$$1 - \left( \frac{\text{Disease rate in complex-applied plot}}{\text{Disease rate in control plot}} \right) \times 100$$

The values indicated in the table were those obtained by inspection on the 18th day from sowing for cucumber and on the 45th day from sowing for eggplant and tomato.

TABLE 2

| Disease tested | Test plot | Incidence (%) | Control value (%) |
| --- | --- | --- | --- |
| Fusarium wilt of cucumber | Complex-applied plot | 4 | 91.3 |
| | Control plot | 46 | — |
| Bacterial wilt of eggplant | Complex-applied plot | 12 | 86.7 |
| | Control plot | 90 | — |
| Fusarium wilt of tomato | Complex-applied plot | 2 | 96.1 |
| | Control plot | 34 | — |

What is claimed is:

1. A method for preparing an immobilized microorganism-complex having antagonistic activity against plant pathogenic microorganisms to control plant diseases which comprises adding an inorganic salt of a metal having a valency of two or more to a liquid containing microorganism cells antagonistic to plant pathogenic microorganisms to obtain treated microorganism cells, drying the resulting cells to form powdered, cationic microorganism cells, mixing the cationic microorganism cells thoroughly with anionic particles of humic acid which has been obtained by extraction from composts to form aggregates resulting from ionic bonding of the humic acid to the cationic microorganism cells, mixing the aggregates with an aqueous solution containing at least 10 W/W % of carrageenan, and then drying the resulting liquid mixture.

2. A method according to claim 1 wherein the microorganism antagonistic to plant pathogenic microorganisms is selected from bacteria, actinomycetes, eumycetes, myxomycetes, lichens or algae.

3. A method according to claim 1 wherein the inorganic salt of a metal having a valency of two or more is selected from calcium chloride, magnesium chloride, barium chloride, ferrous chloride, ferric chloride or manganese chloride, 4. A method according to claim 1 wherein the humic acid is that extracted from compost of rice straw, barley or wheat straw, livestock excretions, bark, sawdust, activated sludge and urban wastes or that extracted from soil.

* * * * *